United States Patent [19]

Rice

[11] Patent Number: 5,066,302

[45] Date of Patent: Nov. 19, 1991

[54] BREAST PROSTHESIS

[76] Inventor: Jean E. Rice, 1409 W. Yakima Ave., Yakima, Wash. 98902

[21] Appl. No.: 514,164

[22] Filed: Apr. 25, 1990

[51] Int. Cl.$^5$ ............................................. A61F 2/52
[52] U.S. Cl. ........................................................ 623/7
[58] Field of Search ................... 623/7, 8; 450/54, 55

[56] References Cited

U.S. PATENT DOCUMENTS

| | | | |
|---|---|---|---|
| 2,482,297 | 9/1949 | Silverman | 623/7 |
| 2,752,602 | 7/1956 | Wilhelm | 2/42 |
| 2,867,818 | 1/1959 | Creamer | 623/7 |
| 3,576,037 | 4/1971 | Klein | 3/36 |
| 3,619,819 | 11/1971 | Mann | 3/36 |
| 3,641,592 | 2/1972 | Den Bleuker | 623/7 |
| 3,811,133 | 5/1974 | Harris | 3/36 |
| 3,845,507 | 11/1974 | Kirby et al. | 623/7 |
| 3,911,503 | 10/1975 | Hankin | 3/36 |
| 4,019,209 | 4/1977 | Spence | 623/7 |
| 4,071,914 | 2/1978 | Silverman | 3/36 |
| 4,125,117 | 11/1978 | Lee | 128/481 |
| 4,356,573 | 11/1982 | Knoche | 3/36 |

*Primary Examiner*—David J. Isabella
*Attorney, Agent, or Firm*—George A. Cashman

[57] ABSTRACT

A one-piece prosthesis for use by a woman who has undergone a mastectomy, the prosthesis comprising the form of a complete breast, without voids therein, and with a supplement extending toward the axilla, and a supplement extending toward the clavicle, each supplement designed to fill a void left by surgery, and further having a band below the breast to underlie the lower band of brassiere, said supplements and band being tapered to a fine edge of avoid the appearance of demarcation lines. The prosthesis is molded of silicone which may contain dye to match skin coloration, and approximates the size, shape, density, resilience and pliability of the natural breast in various chest and cup sizes.

9 Claims, 5 Drawing Sheets

BREAST PROSTHESIS

BACKGROUND OF THE INVENTION

A woman who has had a simple or a radical mastectomy can compensate to some extent by having reconstructive surgery, or by wearing a breast prosthesis. Many women, particularly those who are elderly, would not care to undergo reconstructive surgery, and must wear a breast prosthesis.

Most prostheses seem to be designed by men who do not have an understanding of the requirements for a breast prosthesis that will fit the altered shape of the chest in a way that will be truly comfortable, will give the wearer confidence, and will simulate as closely as possible the graceful, flowing lines of the natural mature breast. For example, most mastectomy patients are past the child-bearing age, and the upper part of the breast, above the nipple, is not full, as with younger women, but is more-or-less concave in that area.

Various designs have been patented that feature a back wall made of material such as plastic or sheepskin that would not feel natural against the skin. Some prostheses have a large hollow at the back. Some prostheses simulate the weight of the breast by having an internal void in which a weight is placed. None of them tries to fill all the voids left by radical surgery with a prosthesis approximating the size, shape, weight, resiliency and pliability of an actual breast.

It is an object of this invention to provide a breast prosthesis that simulates the actual mature human breast in size, shape, density, resilience and pliability, so as to fill a brassiere cup in a natural and balanced manner.

It is a further object of this invention to provide a breast prosthesis that will occupy the voids left by radical surgery, and yet will have edges that are unobtrusive, and will blend in smoothly with the wearer's body lines.

It is a further object of this invention to provide a breast prosthesis that will be comfortable to wear against the skin for extended periods of time.

BRIEF DESCRIPTION OF THE INVENTION

The objects of this invention are achieved by providing a breast prosthesis that is of one piece, is solid in the sense of not having voids therein, and which is manufactured of a material that approximates the average density of the female breast.

The prosthesis is molded of a silicon compound having a specific gravity in the range of 0.94 to 0.99, and preferably having a specific gravity of approximately 0.97. The prosthesis is full and rounded below the nipple, and slightly concave above the nipple. There is a lateral supplement tapering to smaller dimensions in thickness and width, and terminating under the armpit. This lateral or axillary supplement fills a void left by surgery. There is also an upward supplement tapering to smaller dimensions in thickness and width, and terminating under the clavicle. This upward or clavicular supplement fills another void left by surgery. There is a band extending downward below the inferior margin of the breast, the band being designed to fit under the lower band of a brassiere.

The prosthesis is provided with a cover of DACRON, a synthetic fiber or silk or similar slick material to cover the outward portions of the prosthesis, and having a backing of one-hundred-precent cotton or similar non-irritating, non-slip material in the areas where the prosthesis will be in contact with the wearer's skin.

DACRON is a registered trademark of E.I. du Pont de Nemours & Co., Inc..

DETAILED DESCRIPTION OF THE INVENTION

The specification and drawings describe and illustrate a left breast prosthesis. It will be understood by those skilled in the art that a right breast prosthesis may be made by following the teachings herein.

Figure 1:
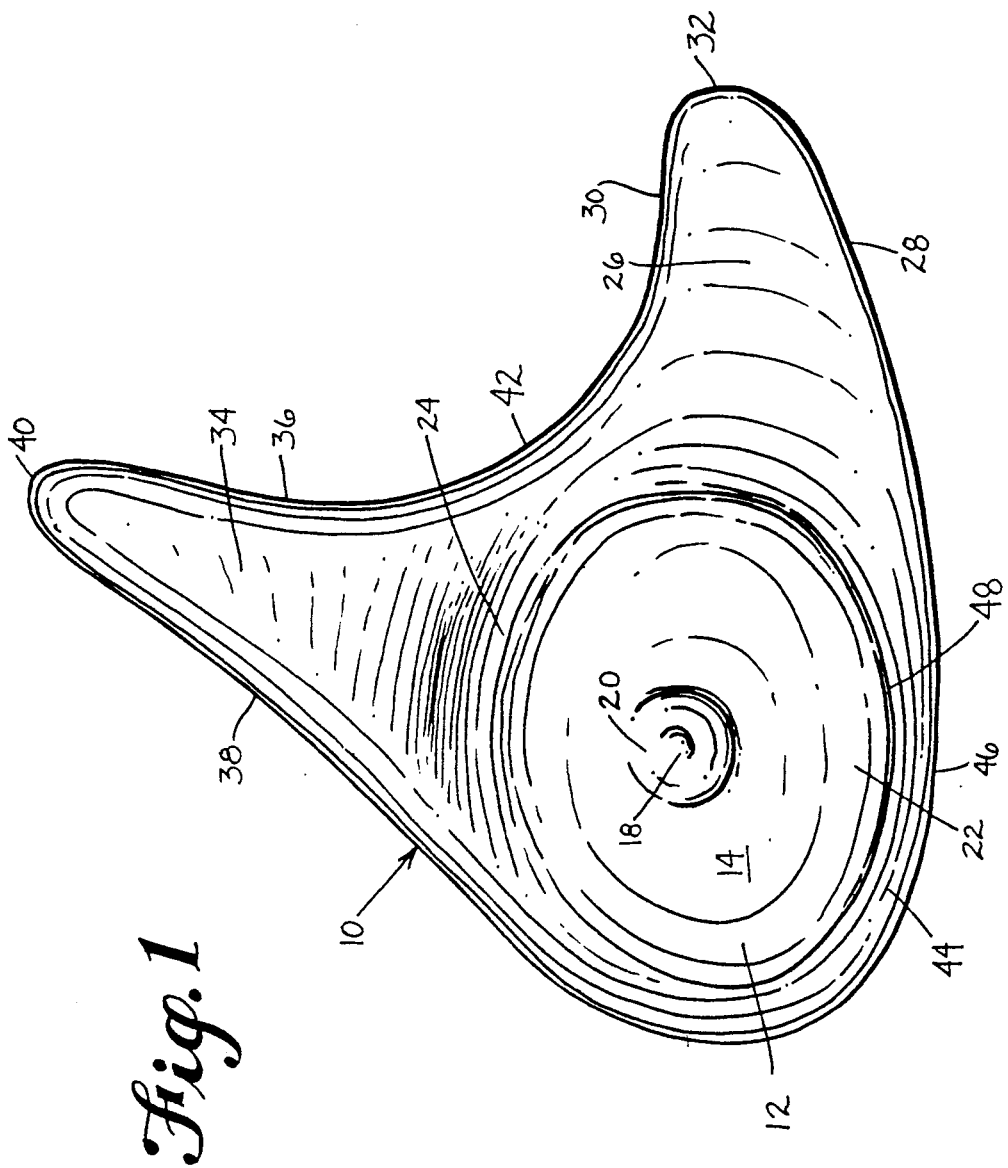
FIG. 1 is a frontal view of the breast prosthesis of this invention.
Figure 2:
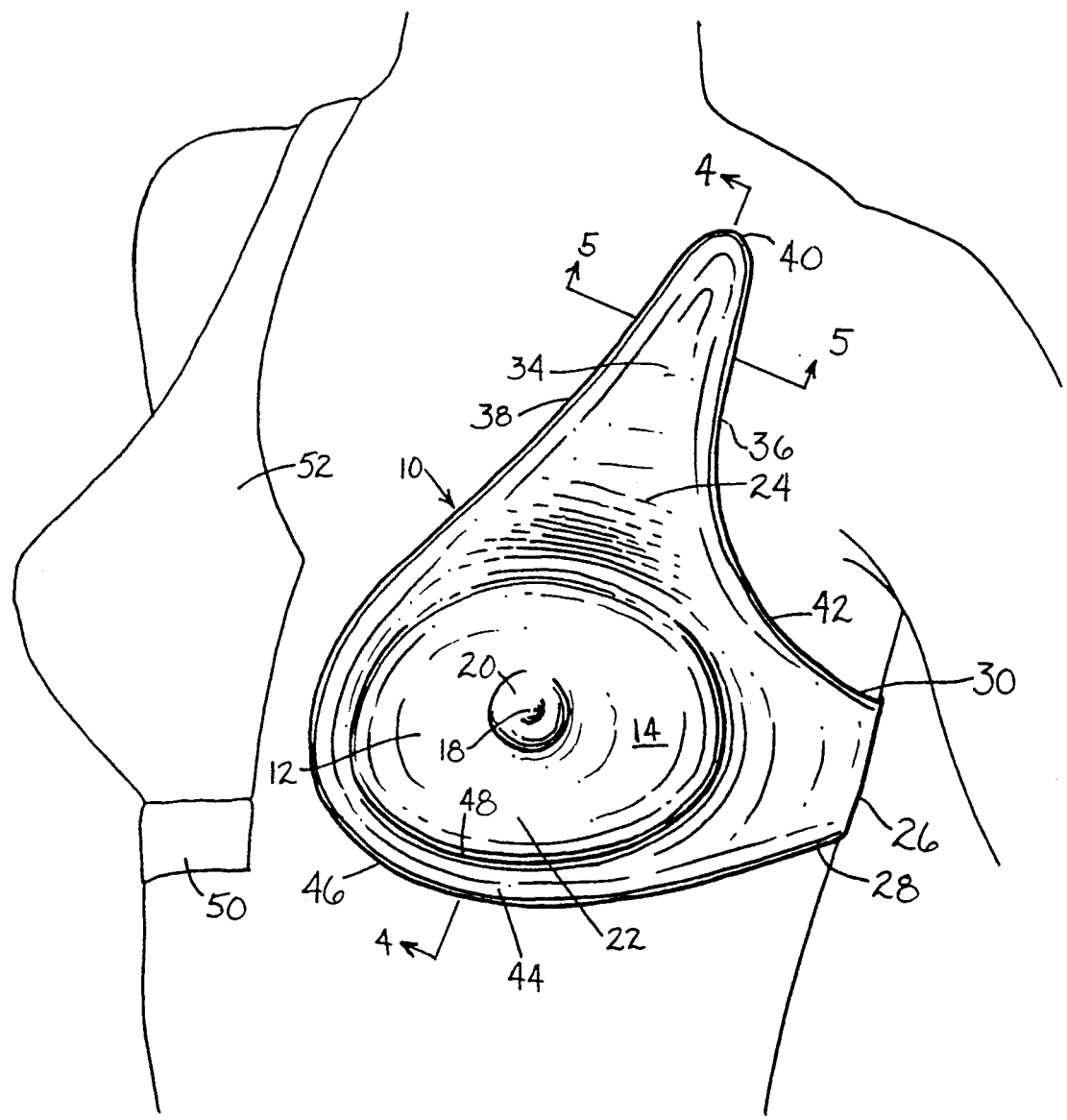
FIG. 2 is a three-quarters frontal view of the prosthesis as it would appear on the wearer.
Figure 3:
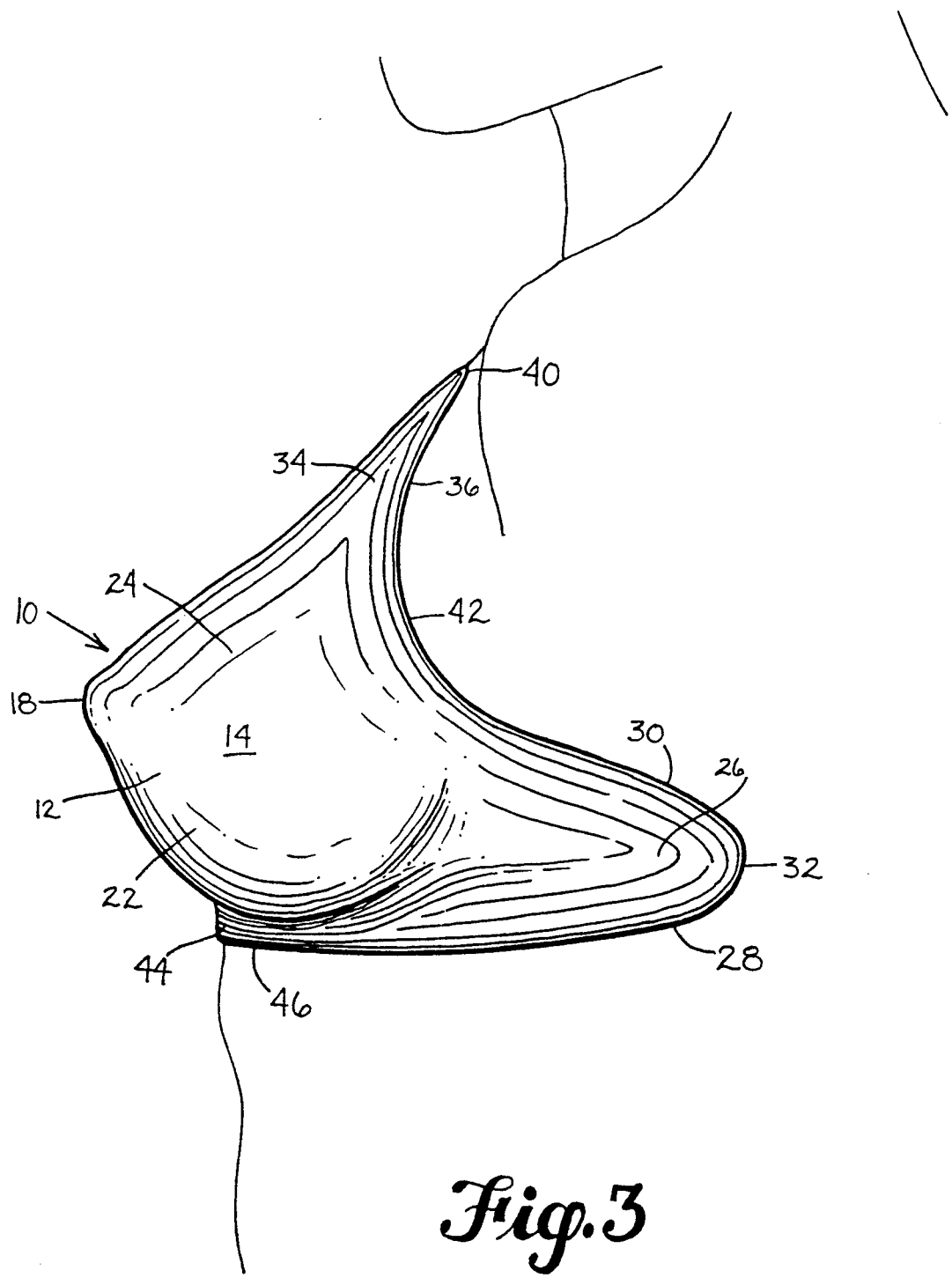
FIG. 3 is a side view of the prosthesis as it would appear on the wearer.

With specific reference to FIGS. 1-3 the prosthesis 10 includes a molded form of a female breast 12, having front surface 14 and back surface 16. Back surface 16 is slightly concave to form a slight vacuum, and to accomodate the rib directly underlying the breast. Nipple 18 surrounded by areola 20 extends outwardly from the foremost portion of front surface 14. It can be seen that lower portion 22 of the prosthesis 10, below nipple 18, is full and rounded, and that upper portion 24 of the prosthesis 10, above nipple 18, becomes slightly concave in profile.

Figure 4:
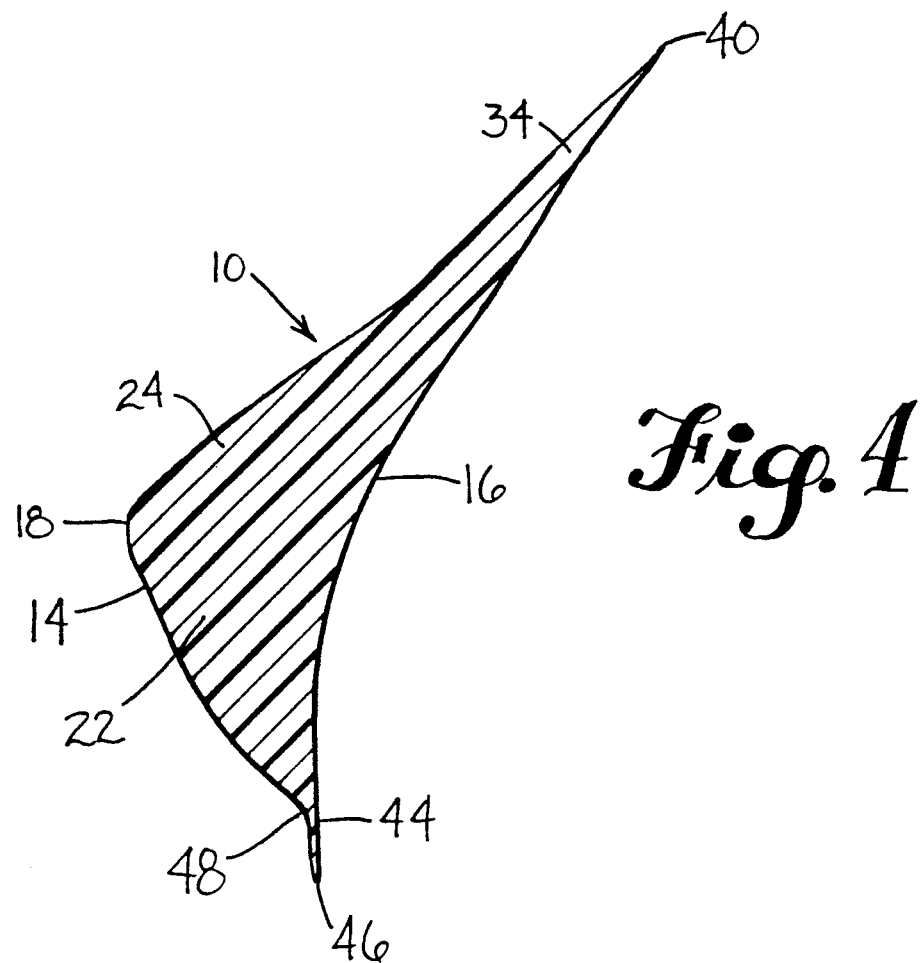
FIG. 4 is a cross-section taken at line 4—4 of FIG. 1.

Axillary supplement 26 is designed to fill the void left by removal of tissue between the breast and the area under the axilla or armpit. Axillary supplement 26 extends laterally from breast 12 and terminates under the wearer's armpit. Axillary supplement 26 tapers in width and in thickness, as may be seen in FIGS. 1 and 3. Edge 28 and edge 30 are joined by rounded edge 32 at the outward end of axillary supplement 26. Edges 28, 30 and 32 are smooth and fine in order to lie flat against the wearer's skin, so as to avoid showing demarcation lines, in the same manner as clavicular supplement 34 illustrated in FIGS. 4 and 5.

Clavicular supplement 34 is designed to fill the void left by removal of tissue between the breast and the clavicle or collarbone. Clavicular supplement 34 extends upwardly, and slightly outwardly, and terminates under the wearer's collarbone. Clavicular supplement 34 tapers in width and thickness, as may be seen in FIGS. 1, 2, 4 and 5. Edge 36 and edge 38 are joined by rounded edge 40 at the outward end of clavicular supplement 34. Edges 36, 38 and 40 are smooth and fine in order to lie flat against the wearer's skin, and to avoid showing demarcation lines.

Edge 42 of prosthesis 10 joins edges 30 and 36 with a smooth curving line.

Figure 5:
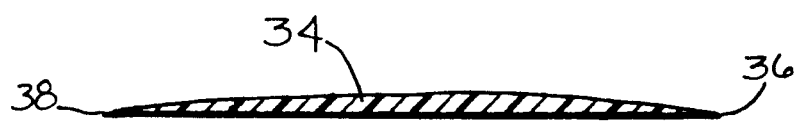
FIG. 5 is a cross-section, to enlarged scale, taken at line 5—5 of FIG. 1.
Figure 6:
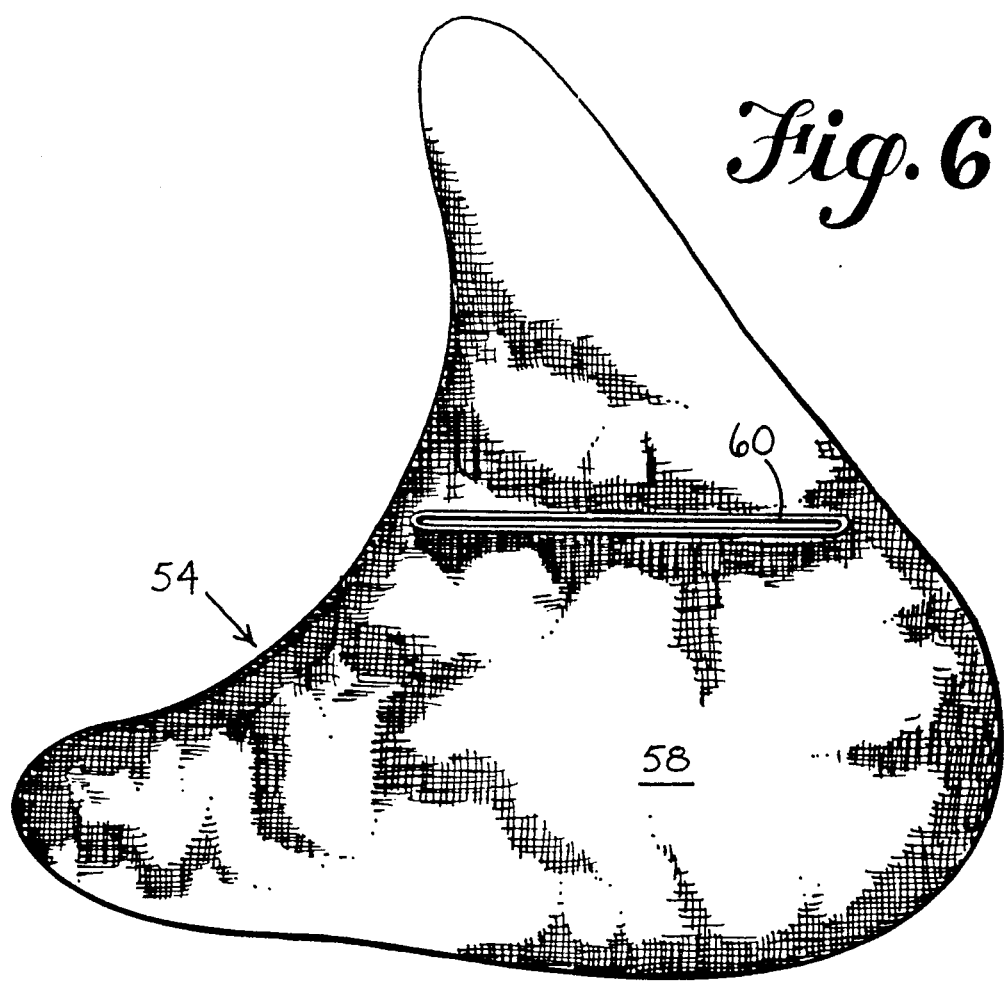
FIG. 6 is a view of the back of the cover used with the prosthesis.
Figure 7:
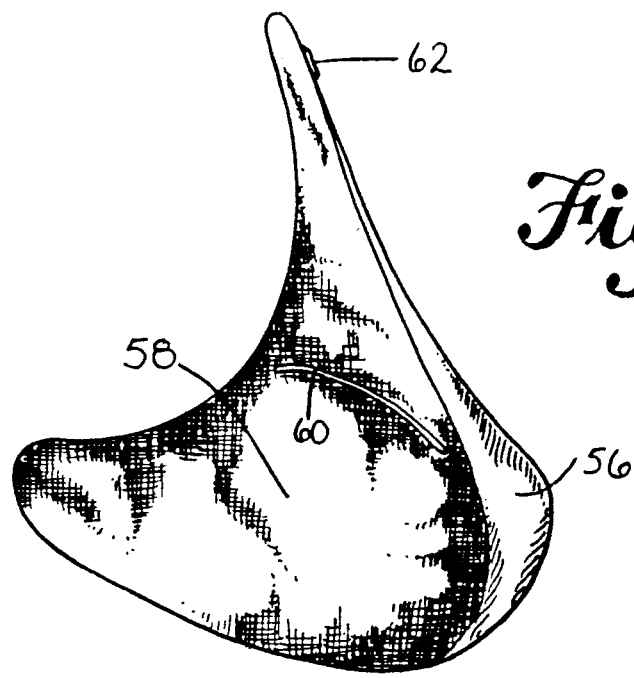
FIG. 7 is a perspective view of the back of the covered prosthesis.

Band 44, which tapers to edge 46 as may be seen in FIG. 5, extends downwardly from inferior margin 48 of breast 12. Edge 46 of band 44 joins edge 28 of axillary supplement 26 with edge 38 of clavicle supplement 34, leaving a sufficient width below inferior margin 48 of breast 12 to underlie fully lower band 50 of brassiere 52.

Prosthesis 10, when in use, has a washable cover 54. Cover 54 comprises front portion 56 which may be made of DACRON, or any similar slick, washable fabric, joined by a cement or similar bond to back portion 58. Back portion 58 may be made of one-hundred-percent cotton, or any similar non-irritating, hypoallergenic, washable fabric. Front portion 56 of cover 54 has the shape of front surface 14 of breast 12, and back portion 58 of cover 54 has the shape of back surface 16 of breast 12. Back portion 58 has opening 60 for nearly the full width of back portion 58, to allow the wearer to remove prosthesis 10 from within cover 54 in order to launder cover 54.

Front portion 56 of cover 54 may be provided with a Velcro dot 62 located near edge 40 of clavicular supplement 34, and a Velcro dot 64 (not shown) located near edge 32 of axillary supplement 26. Dots 62 and 64 cooperate with VELCRO dots which may be placed on the corresponding shoulder strap and side band of the brassiere which will be worn with the prosthesis. VELCRO is comprised of synthetic materials which adhere when pressed together. VELCRO is a registered trademark of Velcro U.S.A., Inc.. The VELCRO dots would be optional with the wearer, because the well-tapered edges of the prosthesis fit closely to the body and tend to remain in place.

Although the prosthesis 10 is not intended to be visible when the wearer is fully clothed, and is not intended to be worn with strapless clothing, it may be manufactured with differing shades of dye to provide a wide variety of skin colors in order to enhance the wearer's sense of comfort. It may be manufactured in chest sizes from 32 to 42, with cup sizes from A through D.

The silicone material of which prosthesis 10 is molded has the proper density, resilience and pliability to simulate the natural breast, to fill and to shape a brassiere cup in the normal manner, and to fill the voids left by surgery in a way that will not be conspicuous, yet will give the wearer a sense of having a full figure.

While this invention is susceptible of ebodiment in different forms, the drawings and the specification illustrate the preferred embodiment of the invention, with the understanding that the present disclosure is to be considered an exemplification of the principles of the invention, and the disclosure is not intended to limit the invention to the particular embodiment described.

I claim:

1. A solid breast prosthesis made entirely of a silicon compound, and comprising:
    a pliable molded form of a complete female breast, said form having an inferior margin forming the edge of the lowermost portion;
    an axillary supplement extending laterally from the form;
    a clavicular supplement extending generally upwards from the form; and
    a retaining band below the inferior margin of the form.

2. The breast prosthesis of claim 1 wherein: the axillary supplement tapers down in width and in thickness to a curved end adapted to terminate below the wearer's clavicle;
    the clavicular supplement tapers down in width and in thickness to a curved end adapted to terminate below the wearer's clavicle;
    the retaining band tapers in thickness to an edge a sufficient distance below the inferior margin of the breast form to match approximately the width of the lower band of a brassiere;
    the tapered shapes of the axillary supplement, the clavicular supplement and the retaining band enabling such elements to lie flat against the wearer's skin.

3. The breast prosthesis of claim 2 wherein:
    the upper edge of the axillary supplement and the outward edge of the clavicular supplement are joined by a smoothly curved edge directed inwardly near an upper outer quadrant of the main body,
    the lower edge of the band is a laterally continuing extension of the lower edge of the axillary supplement at one of its ends; and
    the edge of the band continues below the inferior margin of the main body and continues around a lower inner quadrant of the main body where said band joins the inward edge of the clavicular supplement in a smoothly curved line.

4. The breast prosthesis of claim 1 further including a back wall wherein the back wall is slightly concave.

5. The breast prosthesis of claim 1 wherein silicone compound has a specific gravity in the range of 0.94 to 0.99.

6. The breast prosthesis of claim 1 wherein silicone compound has a specific gravity of approximately 0.97.

7. The breast prosthesis of claim 1 and further comprising:
    a first cover shaped to cover the prosthesis on the side of the prosthesis on which the breast is formed;
    a substantially planar second cover attached around the entire periphery of the first cover, said second cover having an opening therein for insertion and removal of the prosthesis.

8. The breast prosthesis of claim 7 wherein:
    the first cover is a fabric having a smooth surface; and
    the second cover is a hypo-allergenic fabric.

9. The breast prosthesis of claim 7 wherein:
    the first cover is a fabric having a smooth surface; and
    the second cover is a fabric consisting of cotton fibers.

* * * * *